US008916132B2

(12) United States Patent
Kuljis Azocar et al.

(10) Patent No.: US 8,916,132 B2
(45) Date of Patent: Dec. 23, 2014

(54) BENZIMIDAZOLE-DERIVED COMPOUNDS USE AS MARKERS IN THE CASE OF NEURODEGENERATIVE DISEASES

(75) Inventors: Rodrigo Kuljis Azocar, Providencia Santiago (CL); Ricardo Maccioni Baraona, Vintacurea Santiago (CL); Leonel Rojo, Providencia Santiago (CL)

(73) Assignee: Servicios Cientificos Neuroinnovation Ltda, Santiago (CL)

( * ) Notice: Subject to any disclaimer, the term of this patent is extended or adjusted under 35 U.S.C. 154(b) by 514 days.

(21) Appl. No.: 12/737,597

(22) PCT Filed: Jul. 22, 2009

(86) PCT No.: PCT/IB2009/006405
§ 371 (c)(1),
(2), (4) Date: May 26, 2011

(87) PCT Pub. No.: WO2010/013127
PCT Pub. Date: Feb. 4, 2010

(65) Prior Publication Data
US 2011/0300072 A1 Dec. 8, 2011

(30) Foreign Application Priority Data

Jul. 31, 2008 (CL) .................................. 2267 2008

(51) Int. Cl.
*A61K 51/04* (2006.01)
*A61K 49/04* (2006.01)
*G01N 33/68* (2006.01)
*A61K 31/4184* (2006.01)
*A61K 49/00* (2006.01)

(52) U.S. Cl.
CPC ........ *G01N 33/6896* (2013.01); *A61K 31/4184* (2013.01); *A61K 49/0052* (2013.01); *A61K 51/0455* (2013.01)
USPC ......... 424/1.89; 424/1.81; 424/1.85; 424/9.3; 424/9.44

(58) Field of Classification Search
USPC ................. 424/451, 452, 490, 493, 494, 489; 514/277, 315, 336–338
See application file for complete search history.

(56) References Cited

U.S. PATENT DOCUMENTS

| 6,228,400 | B1 * | 5/2001 | Lee et al. ........................ 424/489 |
| 7,541,476 | B2 * | 6/2009 | Heylen et al. ............... 548/302.7 |
| 2006/0018825 | A1 | 1/2006 | Kudo et al. | |
| 2007/0218002 | A1 | 9/2007 | Barrio et al. | |

FOREIGN PATENT DOCUMENTS

WO    WO 2008133884    11/2008

OTHER PUBLICATIONS

Marcel Michiels, et al., Pharmacokinetics and Tissue Distribution of Astemizole in the Dog, EPO Search Report, 1986.
Masahiko Nakamura, et al., Lansoprazole binding to the neutrophils in dextran sulfate sodium-induced rat colitis, EPO Search Report, 2005.
Nobuyuki Okamura, et al., Quinoline and Benzimidazole Derivatives: Candidate Probes for In Vivo IMaging of Tau Pathology in Alzheimer's Disease, EPO Search Report, 2005.
Leonel E. Rojo, et al. Selective Interaction of Lansoprazole and Astemizole with Tau Polymers; Potential New Clinical Use in Diagnosis of Alzheimer's Disease, EPO Search Repor Jan. 1, 2010.
Second Examination Report in EP, 2014.
L. Rojo et al., International Conference on Clinical PET and Molecular Nuclear Medicine (IPET 2007) 2007.
Extended EP Search Report, 2013.
Cooperation Agreement in the Field of Patents, 2009.

* cited by examiner

*Primary Examiner* — Michael G Hartley
*Assistant Examiner* — Jagadishwar Samala
(74) *Attorney, Agent, or Firm* — Gottlieb, Rackman & Reisman PC

(57) ABSTRACT

Use of benzimidazole-derived compounds of formula (I) according to the following structure, wherein x is a heteroatom selected from N, S, O, P, SO, $SO_2$ and $SO_3$, preferably from N, S and $SO_3$ and most preferably from N and $SO_3$; n may be 0 or 1, R1 is a group selected from formula (II) and formula (III) and R2 is a group selected from H and formula (IV) since the aforesaid serves for the production of a formulation used as a specific marker in the case of neurodegenerative diseases and tau pathologies.

15 Claims, 6 Drawing Sheets

BENZIMIDAZOLE-DERIVED COMPOUNDS USE AS MARKERS IN THE CASE OF NEURODEGENERATIVE DISEASES

The present invention relates to radioactively marked benzimidazole-derived compounds that are useful as specific markers for neurodegenerative disorders.

BACKGROUND ART

Alzheimer's Disease (AD) is a disease that is difficult to treat and that requires an early diagnosis to control or reduce its effects. AD is a high impact disease in the public health system and one of the most important dementias. Furthermore, it is the fourth largest cause of death worldwide after cardiovascular disorders. AD's prevalence worldwide in those over 65 years of age reaches 12%. Approximately 100, 000 persons die per year from AD and its cost to the US economy is US$170 million each year (Wimo and Winblad, 2001).

Dementia, a cognitive syndrome characterized by a decrease in cognitive functions, affects an important percentage of this population. Among all the dementias, AD is the most prevalent and with highest incidence. This situation implies a substantial expense for the government, and it has been determined that there has been an increase in the incidence of AD due to the increase in life expectancy. On the other hand, there is a group of related pathologies, the taupathies, which are disorders in which the tau protein, an essential component of the cytoskeleton, aggregates in the brain to form structures called neurofibrillary tangles (NFTs) (Maccioni and Cambiazo, 1995; Maccioni et al., 2001). NFTs are formed by polymeric tau aggregates, a protein that has been investigated in depth for more than 30 years in the context of Alzheimer's Disease (Maccioni et al., 1986; 1995; 2001). These pathologies have no cure to date, but finding a diagnostic procedure for their early detection would allow substantial patient survival and quality of life. Additionally, a procedure and technologies allowing an accurate diagnosis of AD would stimulate the development of therapies to control the disease.

The fast development of neuroimaging and radiopharmaceutical technologies has made important contributions to the understanding of the pathophysiological processes occurring in the human brain possible. However, such approximations in many neurodegenerative disorders, such as AD, are still very non-specific and therefore do not allow accurate diagnosis.

The publications of Klunk et al., (2004), Verhoeff et al. (2004), Glodzik et al. (2005), and Mosconi et al. (2005, 2007), have shed light on some senile plaque markers. However, notwithstanding having been developed some years ago, their clinical application has not been established or implemented. The development of radioligands to obtain in vivo images of Aβ plaques and neurofibrillary tangles (NFTs), whether by PET, SPECT or other technologies, is currently an important and active area of Nuclear Medicine. The design and biological evaluation of agents to obtain Aβ plaque images, whether by PET or SPECT, requires knowledge of the functional-structural relations of these radioligands, which vary from large proteins and peptides such as Aβ and radioactive monoclonal antibodies down to small molecules derived from Congo red, Chrysamine-G, Thioflavin-T, and Acridine Orange. Recent studies have shown that with this type of technology it is possible to obtain in vivo images in humans suggesting both senile plaques and NTFs, although the correlation has not been established. The most useful radiotracers to this date have been relatively small molecules (<600 Da). The development of radioligands to obtain in vivo plaque images of Aβ-amyloid (PAB) and NFTs, whether by PET or SPECT, has been an important and active area in the radiopharmaceutical industry (Mathis et al., 2005). The marking of specific pathological abnormalities will be of great use in the early diagnosis and identification of persons at risk of developing a given disease.

The only compounds that have been tested in humans to detect abnormal structures in the brains of AD patients are the Pittsburg compound (PIB) and FDDNP, which mark senile amyloid plaques. Amyloids, however, are not a pathognomonic sign in the detection of Alzheimer (Maccioni et al., 2001), and its marking lacks specific pathological diagnostic value. PIB is a compound derived from thioflavine T that binds to senile plaques in the brain, composed primarily of amyloid peptides. PIB has been used without success as a diagnostic tool to detect the accumulation of senile plaques in the brains of patients with AD and other dementias. Although PIB can generate images that suggest the layout of senile plaques visualized by means of positron emissions (PET technology), it has practically had no use for AD diagnosis. This is because senile plaques are not pathognomonic of Alzheimer's Disease, i.e., there are healthy individuals with an important amount of senile plaques in their brains that evidence no cognitive deterioration whatsoever. No compound specifically marking NFT lesions formed by tau aggregates has therefore been tested, so that the molecules of this invention are the only products actually able to specifically mark these structures.

To this date, different types of neuroimaging techniques have been tested without positive results as an approximation to the diagnosis and assessment of the evolution of AD and taupathies in time (Mathis et al., 2005, Rusinek et al., 2003, Stoub et al., 2005, Rosen et al., 2005, Godbolt et al., 2006). These techniques include: Computerized Axial Tomography, Nuclear Magnetic Resonance (NMR), both structural (sNMR) and functional (fNMR), Single Photon Emission Tomography (SPECT), and Positron Emission Tomography (PET). This last technique provides information on the glucose brain metabolism. All these neuroimaging techniques have the advantage of being technically non-invasive so that they may be applied on repeated occasions and at distinctive time intervals in order to assess and identify brain anomalies before patients present the full clinical picture (Rusinek et al., 2003). In short, standard diagnostic procedures by means of neuroimagery are not specific to AD, since virtually all efforts to achieve an AD neuroimaging technology have been addressed at amyloid deposits, including the "Pittsburgh compound" (PIB) and the 2-(1-{6-[(2-[F-18]fluoroethyl) (methyl)amino]-2-naphthyl}ethylidene) malononitrile (FDDNP) (Klunk et al., 2004, Mosconi et al., 2007, Small et al., 2007); these detect amyloids as well as NFTs, and therefore do not allow selective visualization. It is not clear from these studies what lesions they intend to visualize (for example 'diffuse' vs. 'complete' plaques, etc.). It is known that the first compound does not visualize NFTs, and the latter can visualize different types of lesions, besides NFTs, so that it is not useful as a diagnostic tool (Mathis et al., 2005, Furomoto, 2007). On the other hand, patent applications PCT/US96/05918; PCT/US98/07889; PCT/JP01/02204 and PCT/JP01/02205 describe compounds that are unable to selectively identify NTFs.

The development of pathology-specific radiomarkers for neurodegenerative disorders is essential not only for the diagnosis but also to monitor new AD therapies. It should be noted that a confirming AD diagnosis can only be made through neuropathological means after a "postmortem" analysis of cerebral tissues. However, there is a possibility of obtaining images of the neurofibrillary tangles (NFTs), the primary histological-molecular sign of AD and taupathies. A powerful tool would thereby be available for definitive in vivo neuropathological diagnosis as well as a method to assess the evolution of AD pathophysiological processes (Lavados et al., 2005, Fernández et al., 2008, Kuljis, 2008). There are some approximations to this need, but until now a fully satisfactory and specific diagnosis tool has not been developed. This has kept the problem of diagnosing AD at an early stage as still be resolved (US2006018825; WO02069965; Okamura, 2004 and 2005). Okamura, for example, has described a set of compounds derived from benzimidazoles to detect Aβ amyloid peptide aggregates, without delving in the study of the use of these benzimidazoles as radiotracers in PET diagnosis by means of the detection of neurofibrillary tangles. However, none of the compounds analyzed by Okamura's group have been used in clinical practice, nor has there been any success in their use in PET imaging, and their preclinical studies could take some time to validate their possible use. They are therefore far from being considered as potential radiotracers to identify NFTs by means of Positron Emission Tomography (PET). In this context, our invention is addressed at compounds that bind with high specificity to tau aggregates and that can be used as pathology-specific radiotracers in the early diagnosis of Alzheimer's Disease.

The possibility of obtaining images of AD neurofibrillary tangles, or of any other pathognomonic proteins will provide medicine with the unprecedented opportunity of a definitive diagnosis that can today only be obtained by means of postmortem neuropathological studies. It would additionally provide the possibility of an early diagnosis, a method to study the evolution of the pathological process and a model to assess specific therapeutic interventions.

A specific neuroimaging diagnosis is therefore required for a given lesion. For this reason, the benzimidazole compounds (BZs) able to bind to aggregate tau in the pathological form present in AD are the most promising radiotracers for the development of PET neuroimaging technology. Even more interesting, the present invention provides known and clinically proven benzimidazoles that bind to tau aggregates. The important benefits derived from this invention are: 1) Specific pathological diagnosis, 2) Early diagnosis and the possibility of a presymptomatic diagnosis of AD, 3) Understanding of the natural evolution of the disease and its pathophysiology, and 4) Ability to directly measure the effects of specific therapies that may be developed in the future. This is because this invention makes it possible to obtain images with $^{18}$F-benzimidazoles molecules, thereby proving its differential affinity for tau in neurofibrillary tangles (NFT) and not with normal or monomeric tau, nor with Aβ peptide aggregates, which makes our technology highly specific and reliable for the definite diagnosis of AD. The benzimidazoles in the present invention have the advantage that they are drugs that are already used in medicine for other purposes and that do not have serious secondary effects in patients.

DESCRIPTION OF THE INVENTION

Figure 1:
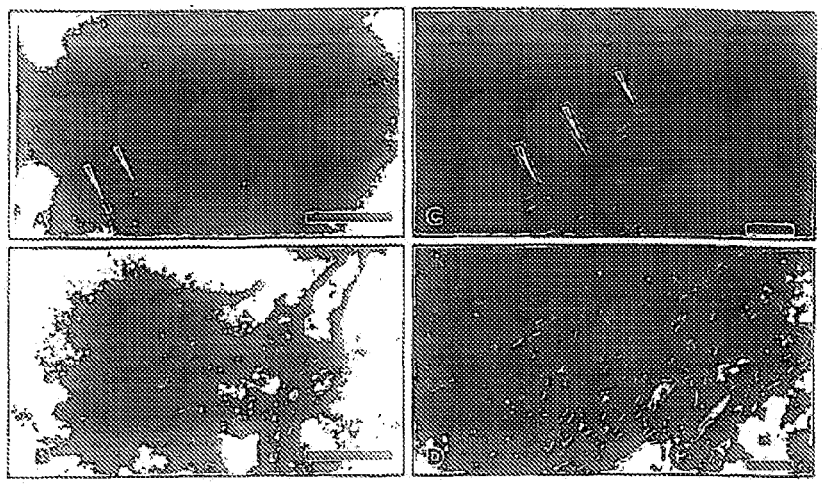
FIG. 1. Electron micrographs of human in vitro tau aggregate filaments and PHFs isolated from AD patients. A and B show human tau filaments (441 aa) induced by 200 μM heparin. (20,000×). C and D show PHFs isolated from AD patients: 80 nm bar. The arrows indicate the torsions in the helicoidal filaments. Straight filaments predominate over helicoidal filaments in heparin induced filaments. It was confirmed that heparin induced filaments are longer than those obtained from human brains and with a lower number of torsions, i.e., most in vitro induced filaments are straight and not helicoidal. Tau filament structural heterogeneity has already been described by several authors (Skravana et al., 2006, Csokova et al., 2003). Considering the structural differences in the in vitro and in vivo formed tau filaments, separate studies were carried out on the interaction parameters for heparin induced filaments and for filaments isolated from AD patients. It is also known that the exposed sites where molecules, such as those described in this invention, bond are the same in both conformations (human tau filaments aggregated in vitro and PHFs isolated from AD patients). However, it is not yet possible to clearly elucidate the mechanisms whereby PHFs are conformed, which would lead to a better understanding of the similarities between both structures.

The present invention relates to benzimidazole derivatives useful in the detection of tau protein deposits as a diagnostic method for neurodegenerative disorders, and tau pathologies, preferably Alzheimer's Disease. The invention, in turn, includes formulations that comprise these molecules, the kit, products and devices containing them. In particular, the invention provides the necessary means for the early diagnosis in its initial stages of the development of neurodegenerative disorders, tau pathologies, preferably Alzheimer's Disease type pathologies.

The invention provides a product which is an excellent tracer to perform diagnosis by means of neuroimaging studies of cerebral damage, such as Positron Emission Tomography (PET), to characterize diseases such as Alzheimer's and others, as well as those disorders that also exhibit tau protein alterations that could be more easily diagnosed by means of the procedure in the present invention.

The invention comprises compounds derived from benzimidazoles of formula (I) according to the following structure:

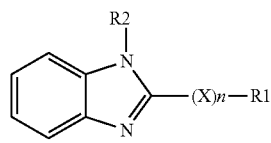

Where:

X is an heteroatom selected from among N, S, O, P, SO, $SO_2$ and $SO_3$; preferably from N, S and $SO_3$, and most preferably from N and $SO_3$;

n may be 0 or 1;

R1 is a group selected from:

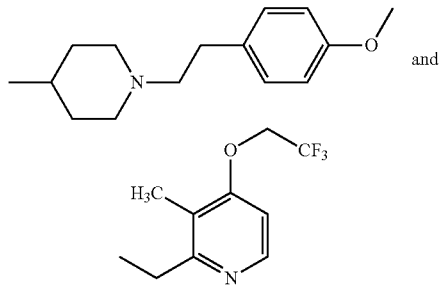

R2 is a group selected from H and:

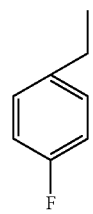

DETAILED DESCRIPTION OF THE INVENTION

The present invention comprises products derived from benzimidazoles (BZs) in the form of formula (I), preferably with BZs substituted in the 2-position, preferably Astemizole and/or Lansoprazole,

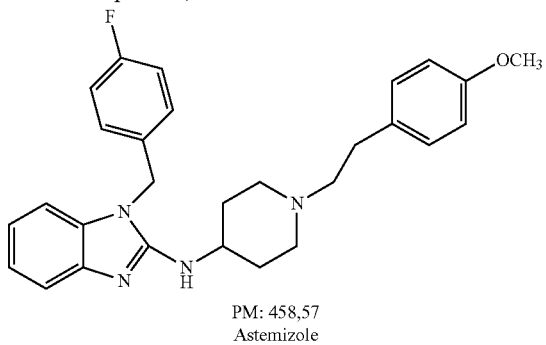

PM: 458,57
Astemizole

-continued

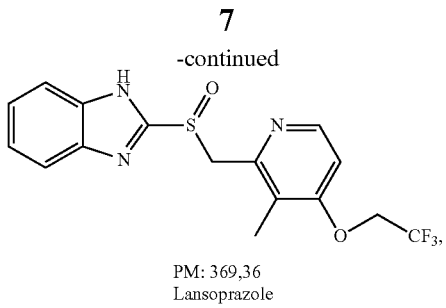

PM: 369,36
Lansoprazole which may be radioactively marked with elements that emit gamma rays such as $^{99m}$Tc, $^{111}$In, $^{67}$Ga, $^{201}$Tl, $^{123}$I and $^{133}$Xe and/or with elements that emit positrons, such as $^{11}$C, $^{13}$N, $^{15}$O and $^{18}$F, and/or with $^{3}$H; the compounds are preferably marked with $^{3}$H and $^{18}$F and/or elements that emit fluorescence, preferably, and without limiting the scope thereof, such known fluorophores may be selected from among FAM, DYXL, Hex, Tet, Joe, Rox, Tamra, Yac, Max, Edans, Cy5, LC670, Fluorescein, Coumarin, Eosin, Rhodamine, Bodipy, Alexa, Cascade Blue, Yakima Yellow, Lucifer Yellow, and Texas Red. These are small molecules that have the property of bonding specifically and with high affinity with the neurofibrillary tangles, and that therefore allow the possibility of detecting those structures by means of neuroimaging studies, as is the case with PET. This property of BZs allows the development of specific neuroimaging studies to visualize the most characteristic lesions of Alzheimer's disease, which is essential not only to improve the diagnosis of the pathologies, but also to develop new treatments by means of tests that allow the identification of new active principles for neurodegenerative disorders.

It has been found, pursuant to this invention, that benzimidazole derivatives of formula (I), preferably radioactive astemizole and/or lansoprazole, are compounds able to bond to the aggregate forms of tau proteins with high affinity. This is of great pharmacological importance since it provides the invention with an enormous potential as radiotracers for neuroimaging, and for the diagnosis of Alzheimer's Disease (AD).

Figure 2:
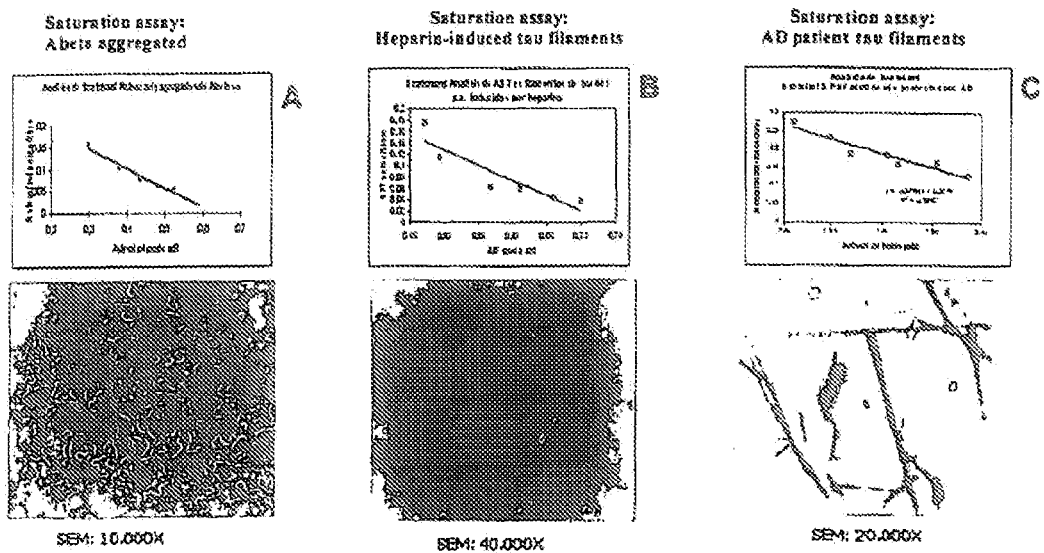
FIG. 2. Scatchard Plots. The Scatchard plots show the saturation studies carried out to assess 3H-Astemizole affinity for Aβ aggregates (A), recombinant human tau filaments (B) and PHFs from AD patients (C). It can be seen in these cases that the molecules in the present invention bond with greater affinity to tau than to peptide Aβ, where the affinity for PHFs is significantly higher than for Aβ.
Figure 3:
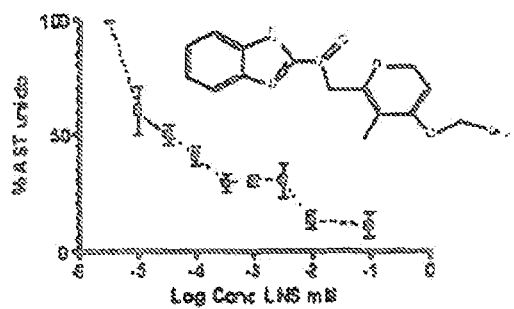
FIG. 3 presents a plot with inhibition studies carried out with lansoprazole on tau filaments isolated from patients with Alzheimer's Disease for N=3±SD, by means of the displacement of marked astemizole. The Ki (nM) calculated for lansoprazole with Tau protein structures can be appreciated in Table 2.

In fact, as may be seen in FIG. 2, the protein-ligand interaction is immensely advantageous for astemizole, since the higher affinity of this agent can be appreciated when bonding to Tau protein systems compared with amyloids. A somewhat equivalent situation can be appreciated with lansoprazole. FIG. 3 shows that lansoprazole at low concentrations displaces astemizole in the Tau protein filaments for Alzheimer patients. This is evidenced in Table 1, which shows the Bmax/Kd values for the interactions of astemizole with Aβ and Tau. It can be seen from this value that astemizole registered a differential affinity for such targets, since it is high for PHF (3.316) in relation to the affinity shown for Aβ fibers (0.057). In effect, astemizole's affinity for PHF is about 60 times larger than for Aβ, which is substantially higher than that described for previously known equivalent compounds. If the information on the State-of-the-Art is considered, US2006/0018825 describes some benzoxazoles, benzothiazoles and benzimidazoles that are structurally different from those utilized in this invention, without quantitatively identifying the agent's bonding affinity to Aβ or tau. On the other hand, Okamura et al., 2005, describe a benzimidazole (structurally different from those utilized in this invention) identified as BP 126, which is shown to have an affinity for Tau fibers of only twice that for Aβ ($EC_{50}$ values in Table 1 in the reference: $EC_{50}$ for Tau=583 nM; $EC_{50}$ for Aβ=1280 nM).

The affinity constants for the compounds in the present invention are found to be in the nM (nanomolar) range, indicating their large affinity for this pathological variant of the Tau protein. This makes their use as specific markers for cerebral tau aggregates possible and they are therefore excellent tracers for neuroimaging studies, for example in Positron Emission Tomography (PET), and for the neuroimaging studies of the cerebral damage that characterizes diseases such as Alzheimer and other taupathies in which the tau protein forms aggregates in the brain or in other organs or tissues.

On the other hand, the present invention provides evidence regarding the drug pharmacokinetics indicating that astemizole and/or lansoprazole molecules reach the brain efficiently and persist for at least 3 hours, thereby allowing the generation of cerebral images for neuroimaging studies, such as, for example, by Positron Emission Tomography (PET).

Figure 4:
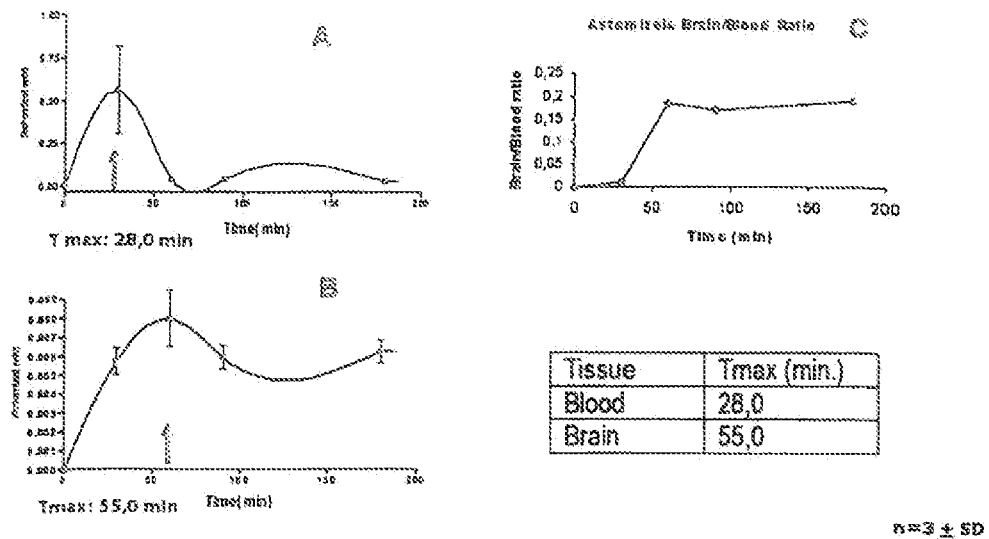
FIG. 4. Comparative Pharmacokinetic Analysis of Astemizole Concentrations in Intracardiac blood (A) and Cerebral Tissue (B) at: 0, 30, 90 and 180 minutes. The brain/blood ratio (C) registered at the measurement times is also shown. The table shows that astemizole reaches cerebral tissues efficiently, with a maximum concentration (Tmax) in blood at 28 minutes, whereas in the brain it is at 55 minutes. It can also be seen that the average life in plasma is less than in the brain, providing an average persistency in the encephalon of at least 3 hours. This makes this molecule an excellent agent for use as a cerebral radiotracer. The tests were carried out with strain C2 albino male rats, with an average weight of 30 grs, which were injected intravenously. The dose was 16 mg/kg. The rats were sacrificed at different times after injection, with intracardiac blood obtained and cerebral tissues extracted for analysis of the concentration of the agent under high performance liquid chromatography coupled with UV (HPLC/UV) detection.
Figure 5:
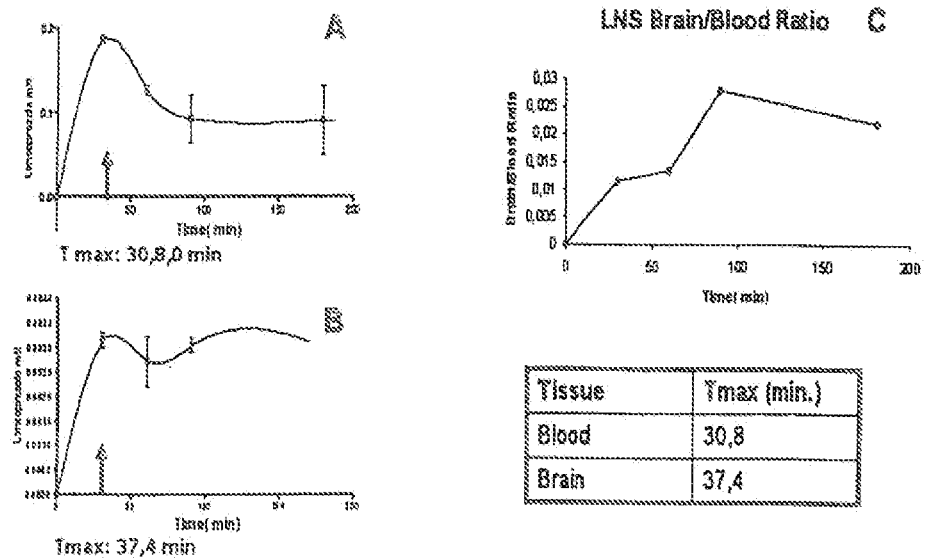
FIG. 5. Comparative pharmacokinetic analysis of Lansoprazole concentrations in intracardiac blood (A) and cerebral tissue (B) at: 0, 30, 90 and 180 minutes. The brain/blood ratio (C) registered at the measurement times is also shown. The table shows that lansoprazole reaches cerebral tissues efficiently, reaching a maximum concentration (Tmax) in blood at 30 minutes, whereas in the brain it is at 37 minutes. It can also be seen that the average life in plasma is less than in the brain. This makes this molecule a compatible agent for use as a cerebral radiotracer. The tests were carried out with strain C2 albino male rats, with an average weight of 30 grs, which were injected intravenously. The dose was 8 mg/kg. The rats were sacrificed at different times after injection, with intracardiac blood obtained and cerebral tissues extracted for analysis of the concentration of the agent under high performance liquid chromatography coupled with UV (HPLC/UV) detection.
Figure 6:
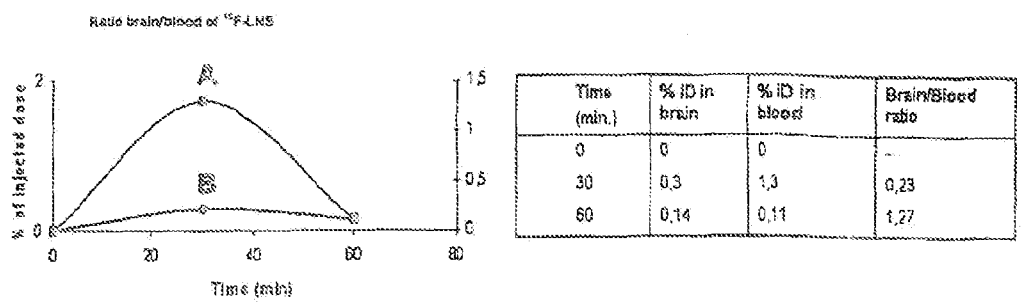
FIG. 6. Comparative Pharmacokinetic Analysis of 18F-Lansoprazole Levels at 30 and 60 minutes in Intracardiac Blood (A) and in the Brain (B), N=3. The table shows the blood brain relation at different times. This shows that the agent will have longer persistency in the brain than in the blood.
Figure 7:
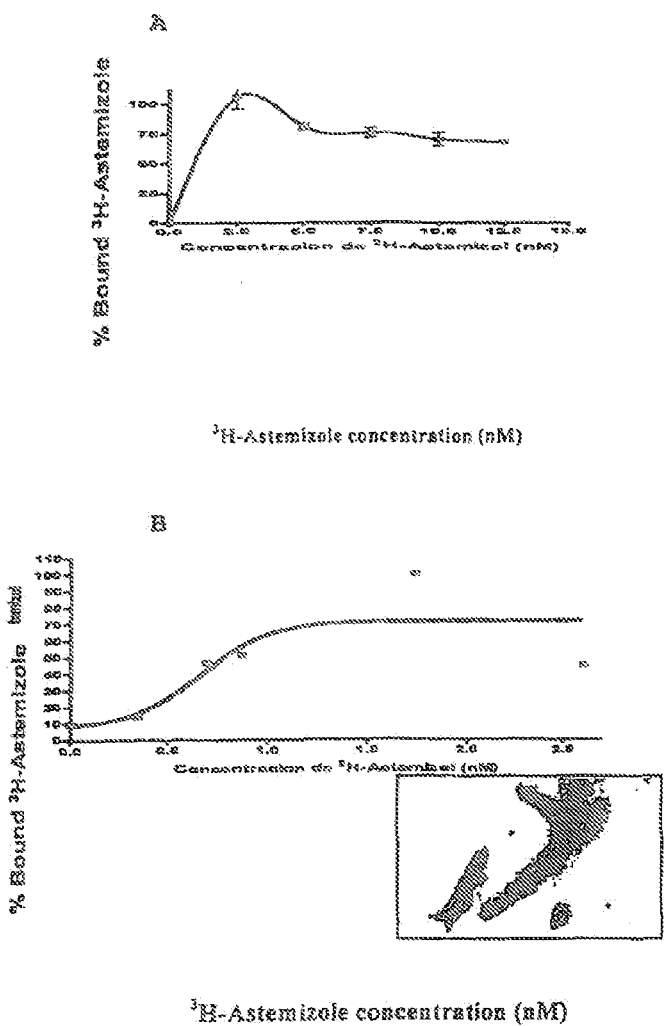
FIG. 7. Shown are 3H-Astemizole affinity plots in relation to tau protein aggregates (A) and Aβ (B). It can be appreciated that 3H-Astemizole has a greater binding affinity to tau protein aggregate forms than to Aβ at low concentrations.

In fact, pursuant to this invention, the proposed agents have longer persistency in the brain and encephalon than in the blood. As shown in FIGS. 4 to 6, astemizole and lansoprazole show an incredible efficiency in reaching and persisting in cerebral tissues, whereas their presence in the blood falls rapidly and notably. These qualities make the proposed compounds in the present invention an excellent candidate with enormous potential as radiotracers for neuroimaging tau dependent neurodegenerative disorders, for which they are of great pharmacological importance since the invention provides molecules that are excellent candidates for the diagnosis of Alzheimer's Disease (AD).

This is due to the fact that this invention facilitates the possibility of marking a specific and pathognomonic AD lesion which would the diagnosis of AD and taupathies with differential diagnosis since:

The benzimidazole molecules in this invention selectively bond to tau proteins much more than to Aβ peptides (FIG. 2 and Tables 1 and 2).

These molecules allow the detection of the presence of aggregate forms of the tau protein, which is not possible with PIB or with other compounds currently in use in human nuclear medicine.

These molecules present advantages in relation to other molecules used to produce brain images, such as glucose, in view of their high affinity for Tau protein aggregates. The most used radiotracer for positron emission imaging is Fluordeoxyglucose. However, its bonding with cerebral tissues is very unspecific, since it concentrates primarily in all cells with high metabolic rates and not in the tau protein macromolecular aggregates such as astemizole and lansoprazole do. Furthermore, in AD there is a drop in the uptake of F-deoxyglucose by cortical neurons.

The in vivo evidence in rats indicates that the concentration of the present invention's molecules marked with $^{18}$F in the brain is high and remains in the brain for at least 3 hours, allowing their use as cerebral radiotracers (FIGS. 4 and 5).

Astemizole and lansoprazole are in addition clinically proven and authorized medical compounds, with abundant clinical evidence in applications different from those proposed herein. Furthermore, from such evidence it would not possible to derive what is proposed in this invention and evidenced in the in vivo and in vitro tests that were performed and included herein as part of the present invention. In fact, Astemizole is an antihistamine drug and Lansoprazole is clinically used as a proton pump inhibitor, whereby these drugs are accepted for medical use, and the present invention relates to a new application that has never before been described for these compounds.

Pursuant to this invention, the techniques wherein the molecules described herein may be utilized are: Computerized Axial Tomography (CAT), Nuclear Magnetic Resonance (NMR), both structural (sNMR) as well as functional (fNMR), Single Photon Emission Tomography (SPECT) and Positron Emission Tomography (PET).

This invention therefore provides a pharmacologically safe and medically proven tool with high affinity and selectivity for Tau protein structures compared to Aβ. This allows the stipulation of an application, method or use for such agents in the identification and diagnosis of neurodegenerative disorders, tau pathologies, preferably Alzheimer's Disease. This allows not only the diagnosis of the manifested disease, but also its early identification considering the fact that Tau is directly related to the development and deterioration of those pathologies, specially AD. These evidences will allow a diagnosis of neurodegenerative disorders in their early asymptomatic stages of pathology, thereby favoring preventive and curative treatments on an anticipated basis for these patients. This can favor improved expectancies for improvement and control of the disease, with substantial improvement in the patient's quality of life, which is unthought-of with current postmortem diagnostic methods. It also allows diagnosis of neurodegenerative disorders when already declared, clinically confirmed and in its advanced stages.

EXAMPLE 1

Appraisal of Benzimidazole Affinity for Tau Protein Aggregates

In order to evaluate benzimidazole's specific affinity for tau protein aggregates, the bonding affinity parameters (disassociation (Kd) and maximum binding (Bmax) constants) were determined for $^3$H-Astemizole for tau aggregates, and the inhibition constants (Ki) were also evaluated for tau protein aggregates in $^3$H-Astemizole displacement tests. The determination of the Kd and Bmax constants is a necessary step prior to the determination of the Ki constants. That is, it is necessary to have the Kd value for a known radioligand in order to obtain the Ki values through inhibition tests and the use of the Cheng-Prusoff equation.

These experiments were carried out using the tau protein obtained from AD patients and synthetic Aβ$_{1-42}$ peptide aggregates obtained from solutions of monomers obtained from AD patients.

1.1. Obtention of the Different Tau Protein and Aβ Peptide Aggregates.

The different proteins were obtained as follows:
a) Helicoidal tau filaments (PHF) were isolated as described by Vinzent and Davies (1992). Briefly, immunoaffinity columns were built based on Protein-A bonded with the MC-1 antibody specific for paired helicoidal filament tau. The antibody's bonding efficiency in the column's stationary phase was >90%. The immunoadsorbent support was deposited in columns and washed with TBS (3 times). The column was then maintained at 4° C. The supernatant (27,000×g) of homogenized brain tissue was loaded in this column at a flow rate of 25 mL/hour. The non-specific bonding was minimized by successive washings with 30 times the column volume using a TBS tampon. The PHFs enriched fractions were dialyzed and stored at −70° C. until their utilization.

b) Amyloid peptide aggregates: synthetic Aβ peptide aggregates were obtained by incubating the peptide in a PBS1X tampon for 7 days. The aggregates were monitored by means of transmission electron microscopy and polyacrylamide gels.

1.2. Determination of the $^3$H-Astemizole Interaction Parameters for Tau Protein and Aβ$_{1-42}$ Peptide Aggregates.

The following protein-ligand interaction parameters were studied to evaluate the affinity of $^3$H-Astemizole for both proteins: disassociation (Kd) and Maximum Binding (Bmax) constants. The dissociation constant (Kd) is a parameter that is inversely proportional to the compound's binding affinity. Bmax is the maximum bonding and indicates the maximum amount of the drug that bonds to a given amount of tau aggregate or Aβ peptide. The following protocol was followed when carrying out these experiments:

Methodology of the Affinity Studies:

Saturation tests with tritiated-AST were carried out to verify the affinity of astemizole (AST) and lansoprazole (LNS) for tau aggregates. The tau polymers (40 mg mL of Alzheimer PHF and 0.01 mg/mL of in vitro filaments) were briefly incubated in the presence of growing concentrations of tritiated-AST (0-2.5-5.0-7.5-10.5-12.5 nM). The mixture was then cold-filtered (4° C.) with Watman GF/B filters. The filter was dried at room temperature and the radioactivity retained in the filter was then measured with a TRICARB-2100 TR scintillation counter in the presence of 2 mL of scintillation solution.

Inhibition Studies:

The interaction of Lansoprazole with tau filaments (PHFs and heparin induced filaments) was studied by means of the displacement of tritiated Astemizole. This was carried out by incubating 40 ug/mL of Alzheimer PHF and 0.01 mg/mL of in Vitro filaments in a series of increasing dilutions of LNS (0.09 to 0.000003 mM). The mixture was then cold-filtered (4° C.) with Watman GF/B filters. The GF/B filter was dried at room temperature and the radioactivity retained in the filter then measured with a TRICARB-2100 TR scintillation counter in the presence of 2 mL of scintillation solution.

FIG. 2 shows the experiment images obtained by means of electron microscopy and the Scatchard plots showing the analysis of the data. Table 1 shows a comparative analysis of the saturation data. These results indicate that $^3$H-Astemizole has greater binding affinity with tau protein aggregates than with Aβ$_{1-42}$ peptide aggregates, since the maximum Kd/Bmax relation for the bonding with human tau protein aggregates (PHFs) was nearly 60 times greater than for $_{Aβ1-42}$ peptide aggregates. This supports the use of the compounds in the present invention as radiotracers for specific pathologies, in contrast with the "PIB compound" that bonds more with Aβ than with the tau PHFs. Although the Bmax/Kd values in the present invention are not significantly high, as would be expected under optimal conditions with a Bmax/Kd relation near 10, the compounds here described have high potential as cerebral radiotracers. This is reinforced by evidence that the molecular targets, such as NFTs in patients with AD (Mathis et al., 2004, Okamura et al., 2005, Klunk et al., 2005), are very abundant in the cerebral parenchyma in the pathological cases explored in this invention. The affinity values set forth herein are therefore sufficient for a successful diagnostic and preventive implementation.

TABLE 1

$^3$H-Astemizole Interaction Parameters for Tau
Protein and Aβ$_{1-42}$ Peptide Aggregates.

| Parameter | Tau Protein Aggregates | Aβ$_{1-42}$ Peptide Aggregates |
|---|---|---|
| Kd | 3.94 nM | 2.1 nM |
| Bmax | 13.07 nM | 0.12 pmol/nmol Aβ$_{1-42}$ |
| Bmax/Kd Index | 3.316 | 0.057 |

1.3. Appraisal of Benzimidazole Affinity for Human Tau Protein Aggregate.

Lansoprazole affinity for human tau protein aggregates was evaluated by means of $^3$H-Astemizole displacement tests. These tests were carried out pursuant to the aforementioned protocol.

Table 2 shows the results for the inhibition studies and the Ki constant obtained for each molecule by means of the Cheng-Prusoff equation (Okamura et al., 2004, 2005).

TABLE 2

Inhibition constants (Ki) obtained from displacement tests
of $^3$H-Astemizole in human tau protein aggregates.

| Drug | Ki(nM) | Molecular Target | Source |
|---|---|---|---|
| Lansoprazole | 833.3 | Alzheimer PHF | Authors' Data |
| Lansoprazole | 2.7 | Tau Filaments in Vitro | Authors' Data |
| BF168 | 6.4 | Aβ Fibers | Okamura et al., 2005 |

It can be seen that lansoprazole exhibits a Ki significantly higher than that shown by other state-of-the-art compounds. Lansoprazole has a greater binding affinity (Ki 2.7 nM) than BF 168 (Ki 6.4 nM) for tau protein aggregates.

Notwithstanding the foregoing, any value in the nM range is potentially useful as a radiomarker for a macromolecular aggregate or receptor present in the cerebral parenchyma.

Figure 12:
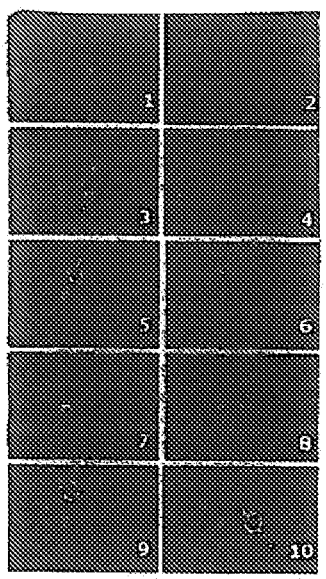
FIG. 12 shows spectrographic representations of each of ten preferential configurations of astemizole bioinformatic tests, which correspond to the data shown in Table 3.

To complement the aforementioned evidence, astemizole bioinformatic tests were undertaken to carry out a Docking study with the Autodock® program. These confirm that the present invention registers favorable binding energy values for this tau ligand, supporting the high affinity that is seen in the other evidence reported herein. Table 3 shows the predictive values for 10 preferential configurations of the PHF-Tau interaction with astemizole modeled with the Autodock® program, numbered 1 through 10, which additionally provides a comparison with the ligand binding energy for some pharmaceutical products with high affinity for the glutamate mGlu4 and mGLu7 receptors obtained with the same program (Yanamala et al., 2008). FIG. 12 shows spectrographic representations of each of the numbered entries. This summarizes the data obtained from the bioinformatic Docking analysis for astemizole and the PHF-Tau-387DHGAE391 pronase resistant fragment, whose crystalline structure is perfectly known since it is exposed in the paired tau protein filaments as described by Novak et al., 1989. Due to tau's structural qualities, the crystallization of the entire protein has not been achieved. The data indicates that astemizole registers a high affinity for the 387DHGAE391 fragment, whereas metronidazole exhibits values that are less favorable. Lower binding energy values are more favorable.

TABLE 3

Site of interaction between Asternizole and PHF-tau:
Bioinformatic analysis (Autodock (Energies))

| | Ligand | Binding Energies Autodock (Kcal/mol) | Receptor | Species | Reference |
|---|---|---|---|---|---|
| 1 | Astemizole | −9.21 | TAU 387DHGAE391 | Human | Author's data |
| 2 | Astemizole | −9.09 | TAU 387DHGAE391 | Human | Author's data |
| 3 | Astemizole | −8.97 | TAU 387DHGAE391 | Human | Author's data |
| 4 | Astemizole | −8.14 | TAU 387DHGAE391 | Human | Author's data |
| 5 | Astemizole | −8.13 | TAU 387DHGAE391 | Human | Author's data |
| 6 | Astemizole | −8.04 | TAU 387DHGAE391 | Human | Author's data |
| 7 | Astemizole | −7.85 | TAU 387DHGAE391 | Human | Author's data |
| 8 | Astemizole | −7.84 | TAU 387DHGAE391 | Human | Author's data |
| 9 | Astemizole | −7.81 | TAU 387DHGAE391 | Human | Author's data |
| 10 | Astemizole | −7.55 | TAU 387DHGAE391 | Human | Author's data |
| | Metronidazole | −2.15 | TAU 387DHGAE391 | Human | Author's data |
| | PHCC | −6.16 | mGluR4 | Human | Yanamala et al., 2008 |
| | AMN82 | −7.56 | mGluR7 | Human | Yanamala et al., 2008 |

EXAMPLE 2

In Vitro Evaluation of the Ability of Benzimidazoles to Cross the Hematoencephalic Barrier This evaluation was carried out for the compound analyzed in Example 1.3. The analyzed parameters were: specific permeability (Sp), this is an indicator of the compound's ability to cross the hematoencephalic barrier (HEB) by passive diffusion, and the partition coefficient (LogP), which corresponds to the partition coefficient of the compound between Octanol and the pH 7.4 phosphate tampon, which is a predictive element for the compound's penetration of the HEB. The determination of the Sp values was carried out as described by Adveef and Tsinman, 2006.

The Parallel Artificial Membrane Permeability assay (PAMPA) is based on the ability of compounds to diffuse from a donor compartment through a Polyvinylidene Fluoride Membrane Filter (PVDF) covered with a phosphatidylcholine solution at 20% towards a second acceptor compartment, which is analyzed. Likewise, a comparative analysis was undertaken with control substances, utilizing Thiopental (40 ug/mL) as a positive control and Clidinium Bromide (800 ug/mL) as a negative control. The quantification was carried out by means of spectrophotometry, using pans 1 mm in length and with a capacity of 300 uL.

The LogP values were obtained by utilizing the protocol described by Cheng et al., 2006, for other potential cerebral imaging radiotracers.

Briefly, the partition coefficient (log $P_{o/w}$) was determined in a pH 7.4 tampon solution, adjusted with 0.1 M sodium hydroxide. The organic phase utilized octanol saturated with the pH 7.4 tampon solution. A 1 mg/mL solution of the drug in methanol was prepared. Dilutions with concentrations ranging from 0.02 to 0.4 mg/mL were prepared from these solutions. Then 0.5 µl to 0.1000 µl portions were taken from each of these previously prepared stock solutions in 25 mL volumetric flasks, with the volume completed with the tampon pH 7.4. 25 ml of octanol where then measured and placed in three decantation funnels, with the previously prepared solutions added to each, mixing both phases by vigorous agitation during two minutes. They were then allowed to set for 48 hours allowing for complete separation of the phases. Both phases are separated once equilibrium had been reached. The aqueous phase was centrifuged during 3 minutes to ensure complete separation of the phases. The entire process was carried out at a temperature of 25° C. The quantification was carried out with a UVN spectrophotometer. Table 4 indicates the values obtained for Sp and LogP coefficients for the benzimidazoles analyzed pursuant to this invention.

TABLE 4

Specific permeability (Sp) and partition (LogP) coefficients obtained from the benzimidazoles under study.

| Drug | Coefficient (Sp) | CNS Transport | LogP Coefficient | CNS LogP |
|---|---|---|---|---|
| Astemizole | 1.47E−04 | Positive | 5.57 | Favorable |
| Lansoprazole | 3.63E−05 | Positive | 1.47 | Favorable |
| Clidinium Bromide | 2.90E−08 | Negative | −0.092 | Unfavorable |
| Thiopental | 1.70E−05 | Positive | 1.4 | Favorable |

CNS LogP means the Partition Coefficient in relation to its ability to cross the hematoencephalic barrier (HEB). The results obtained indicate that Astemizole and Lansoprazole are the compounds with the best liposolubility profiles to be considered as potential cerebral tracers since they efficiently cross the phospholipid membranes. This does not change the molecule's physicochemical properties.

EXAMPLE 3

Evaluation of the Astemizole and Lansoprazole In Vivo Pharmacokinetics in Animal Models The Lansoprazole and Astemizole compounds were analyzed by high-performance liquid chromatography (HPLC) associated with the detection of UV under chromatographic conditions adapted from the method described by Kanazawa et al., 2002.

FIGS. 4 and 5 show the pharmacokinetic experimental results for the Lansoprazole and Astemizole compounds. These results evidence that Astemizole (FIG. 4) efficiently reaches the cerebral tissues (C), the time for maximum concentration (Tmax) is at 28 minutes in blood and 55 minutes in the brain, which is compatible with its potential as a PET radiotracer since Fluor 18's half-life is 120 minutes. It was also observed that the Astemizole's average life in plasma is less than in the brain. This shows a permanency in the encephalon of least 3 hours, which is compatible with its use as a cerebral radiotracer (Ono et al., 2006, Mathis et al., 2004, 2005).

FIG. 5 shows that Lansoprazole efficiently reaches cerebral tissues (C), with the time for maximum concentration (Tmax) at 30 minutes in blood and 37 minutes in the brain, which is compatible with its use as a PET radiotracer since Fluor 18's half-life is 120 minutes. On the other hand, it can be observed that Lansoprazole's average life in plasma is less than in the brain, possibly because of the liver's high metabolic rate and the enzymes that circulate in the plasma, in contrast with what occurs in cerebral tissues, which constitute a highly lipidic pharmacokinetic compartment that eliminates drugs more slowly.

The provided information clearly favors and evidences that the compounds presented pursuant to the present invention are useful for preventive diagnostic applications (in the early stages of neurodegenerative pathologies) or as confirming diagnosis in advanced stages, without requiring a postmortem confirmation as is currently the case. Considering the abundant clinical evidence for these molecules in other pathologies, the proposed use in this case is surprising and highly advantageous in relation to that shown for structurally equivalent molecules in the State of the Art.

Bio-distribution experiments for the radioactively marked Lansoprazole compound ($^{18}$F-Lansoprazole) were also undertaken. The results of the bio-distribution brain/blood assays are shown in FIG. 6. It can be seen in the figure that $^{18}$F-Lansoprazole reaches the brain at 0.3% at 30 minutes and drops to 0.14% by 60 minutes. The brain/blood bio-distribution relations at both times were 0.23 and 1.27, respectively, implying higher product persistency in the brain than in the blood. These results are in agreement with what is observed when analyzing Lansoprazole's pharmacokinetics without radioactive marking.

EXAMPLE 4

Figure 8:
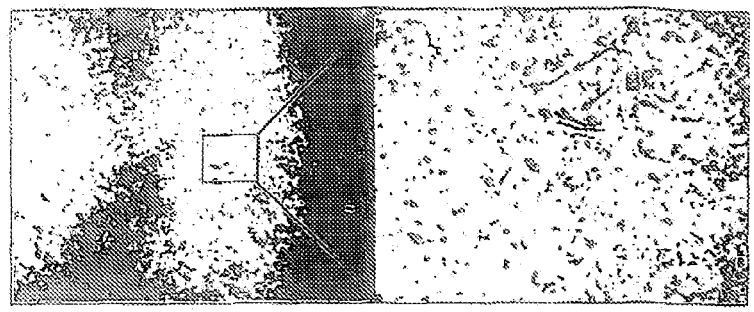
FIG. 8. Shown are fine sections of the hippocampus (20 μm) analyzed for immunohistochemistry with anti-tau phosphorylated antibodies (PHF-1) showing the presence of abundant neuritic (A) type lesions and neurofibrillary tangles (B) in a patient with an AD clinical diagnosis (PHF1).
Figure 9:
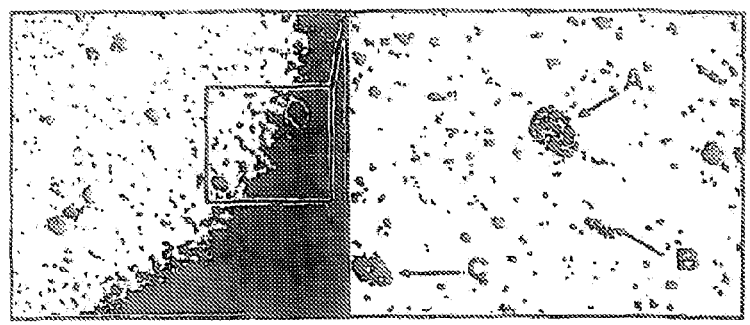
FIG. 9. Shown are fine sections of the hippocampus (20 μm) analyzed for immunohistochemistry with Aβ anti-peptide antibodies (6E10) showing the presence of abundant senile plaques (A, B, C) in a patient with an AD clinical diagnosis (PHF1).

Evaluation of Benzimidazole Fixation in the Neurofibrillary Tangles (NFTs) in Fine Brain Sections of Human Alzheimer Patients The present invention shows in preliminary studies that Astemizole and Lansoprazole bond to the NFTs structures in the postmortem brains of patients with AD. This was evidenced by means of autoradiographic and fluorescent studies. Pursuant to this, the presence of NFTs and senile plaques in the cerebral cortex sections of patients with an Alzheimer's Disease clinical diagnosis was verified in order to assess the use of the present invention in patients. This evaluation was carried out by means of immunohistochemistry with antibodies specific for senile plaque, 6E10 antibody reactive against 6-13 residues of Aβ peptide, and the tau-specific PHF1 antibody. The results are shown in FIGS. 8 and 9.

The purpose sought in these tests was to show the co-localization evidence of these antibodies with the implementation of the radioactively or fluorescently marked molecules of the present invention, and to therefore graph the diagnostic application registered by the invention hereby proposed.

In short, postmortem brains of patients with a proven clinical diagnosis of Alzheimer's Disease are set in formalin at 10%, with slices with sections varying from 5 to 200 µm made, preferably with 20 µm. These slices are incubated in benzimidazoles marked pursuant to the present invention and afterwards incubated with the specific 6E10 and PHF1 antibodies to determine the co-localization of the marker in the tau protein structures of the cerebral sections under study.

Figure 10:
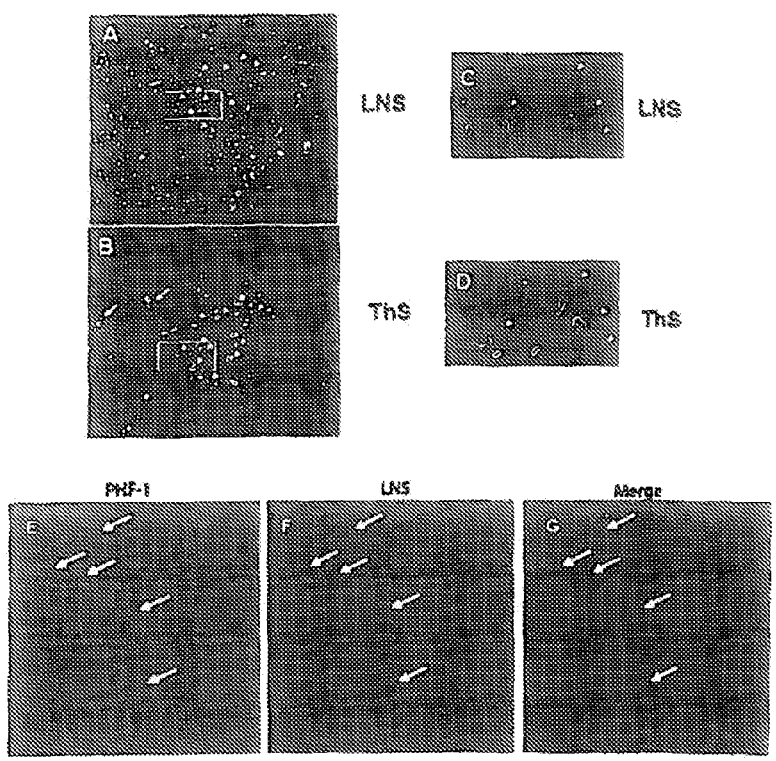
FIG. 10. Shown is a test on postmortem brains from patients with an Alzheimer's Disease clinical diagnosis according to NINCDS-ADRDA criteria for at least 3 months (Dubois et al., 2007), in which marked compounds were used pursuant to the present invention for the selective and specific identification of filamentary tau protein aggregates compared with amyloid structures. Marking with the drug evidenced a co-localization of the markings for the two benzimidazole drugs with the tau protein aggregates in the neurofibrillary tangle type pathological structures. Images A and C, show Lansoprazol fluorescent staining of Tau protein aggregates (arrowhead). Figure G shows col-localization of antibodies specific for Tau (PHF-1) and staining with Lansoprazol, both markings are shown separately in figures E and F, respectively. Tau aggregates are marked with arrow. However, the drugs did NOT show co-markings on the senile plaques formed by the amyloid component (images B and D, staining with thioflavin shows senile plaques (arrows) and Tau aggregates). As a negative control, the control images without the drug markings did not show reactivity. These evidences confirm that the products in the present invention are useful in the diagnosis of neurodegenerative disorders and tau pathologies, preferably Alzheimer's disease.
Figure 11:
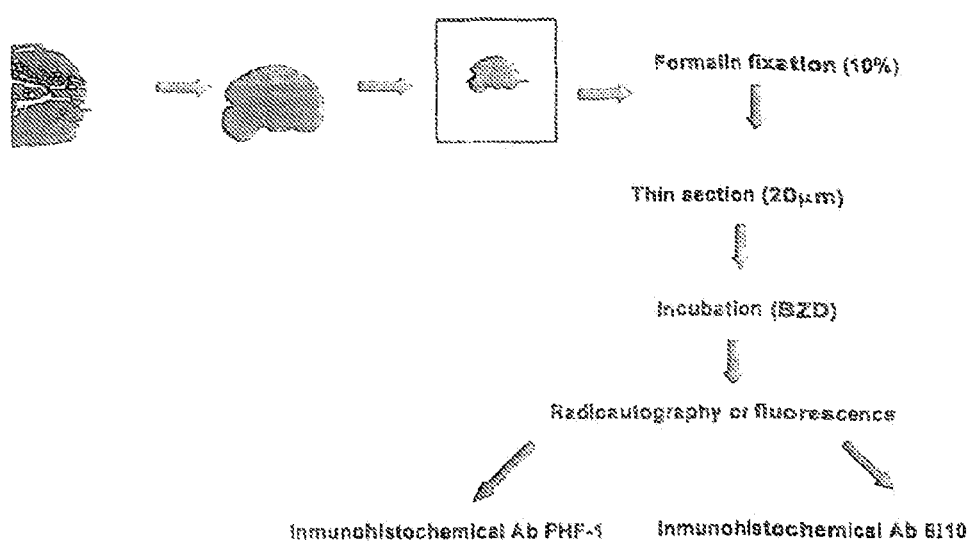
FIG. 11 shows a representation of the procedure to carry out the identification tests with the compounds in this invention on postmortem brains of patients with a clinical diagnosis of Alzheimer's Disease.

As shown in FIG. 10, it may be seen that in patients treated pursuant to the aforementioned process, astemizole and lansoprazole efficiently and selectively mark those sectors positive for tau, instead of those sectors positive for Aβ, in accordance with what is shown in the studies with the aforementioned antibodies. This clearly evidences that the present invention supports applications with said benzimidazoles as diagnostic agents for neurodegenerative disorders and taupathologies such as Alzheimer's Disease.

Two different technologies for the co-localization of marked astemizole or lansoprazol to identify the pathological structures in the neurofibrillary tangles in the postmortem brains of Alzheimer patients are utilized in carrying out the aforementioned studies: 1) Marking with tritiated benzimidazoles following the protocol described in detail in FIG. 10, and 2) Fluorescent marking with benzimidazoles. For practical purposes and as part of the examples, the co-localization of marked tau with fluorophore conjugate antibodies with the localization of the fluorescently marked drug is analyzed. The co-localization of both drugs with the tau aggregated structures in the hippocampus region, entorhinal cortex and nucleous of Meynert in the postmortem brains with Alzheimer's Disease was reviewed. On the other hand, the marked drug did not fix itself to any type of structures or other types of unrelated structures (amyloid aggregates or plaques for example) in control sections of healthy brains of subjects of the same age as those for the analyzed Alzheimer brains. This occurs since the healthy brain sections do not evidence lesions of the neurofibrillary tangle type formed by pathological tau. With this evidence we demonstrate the specificity of benzimidazoles of the present invention for their use as a second application in the development of a diagnostic method with PET technology for the early and asymptomatic determination of Alzheimer's Disease.

RELEVANT REFERENCES

Adveef and Tsinman, 2006 PAMPA—A Drug Absorption in Vitro Model 13. Chemical Selectivity due to Membrane Hydrogen Bonding: In Combo Comparisons of HDM-, DOPC-, and DS-PAMPA Models. Eur J Pharm Sci. 2006; 28:43-50. Epub 2006 Feb. 14.

Dubois, B, Feldman, H, Jacova, C. Research Criteria for the Diagnosis of Alzheimer's Disease: Revising the NINCDS-ADRDA Criteria. Lancet Neurol 2007; 6: 734-46.

Fernandez J, Rojo L, Kuljis R, Maccioni R B. The Damage Signal Trigger Hipothesis of Alzheimer's Disease Pathogenesis. Journal of Alzheimer' Disease. 2008, 14: 329-333.

Lavados M, Farias G, Rothhammer F, Guillon M, Mujica M, Maccioni C, Maccioni R B. ApoE Alleles and Tau Markers in Patients with Different Levels of Cognitive Impairment. Archives of Medical Research 2005, 36: 474-479.

Klunk W E, Engler H, Nordberg A, Wang and, Blomqvist G, Holt D P, Bergström M, Savitcheva I, Huang G F, Estrada S, Ausen B, Debnath M L, Barletta J, Price J C, Sandell J, Lopresti B J, Wall A, Koivisto P, Antoni G, Mathis C A, Långström B. (2004). Imaging Brain Amyloid in Alzheimer's Disease with Pittsburgh Compound-B. 1: Ann Neurol. 2004 March; 55(3):306-19.

Maccioni R. B., L. Barbeito and J. P. Munoz (2001) The Molecular Bases of Alzheimer's Disease and other Neurodegenerative Disorders". Arch. Medical Research 32: 367-381.

Mathis C A, Klunk W E, Price J C, DeKosky S T. (2005). "Imaging Technology for Neurodegenerative Diseases: Progress toward Detection of Specific Pathologies". Arch Neurol. February; 62(2):196-200.

Okamura N, Suemoto T, Shimadzu H, Suzuki M, Shiomitsu T, Akatsu H, Yamamoto T, Staufenbiel M, Yanai K, Arai H, Sasaki H, Kudo Y, Sawada T. (2004). Styrylbenzoxazole Derivatives for In Vivo Imaging of Amyloid Plaques in the Brain. J. Neurosci. March 10; 24(10):2535-41.

Okamura N, Suemoto T, Furumoto S, Suzuki M, Shimadzu H, Akatsu H, Yamamoto T, Fujiwara H, Nemoto M, Maruyama M, Arai H, Yanai K, Sawada T, Kudo Y. (2005). "Quinoline and Benzimidazole Derivatives: Candidate Probes for In Vivo Imaging of Tau Pathology in Alzheimer's Disease". J. Neurosci. November 23; 25(47):10857-62.

What is claimed is:

1. A pharmaceutical formulation for neuroimaging diagnosis of neurodegenerative disorders and tau pathologies, including tau protein deposits, said formulation comprising benzimidazoles of formula (I) according to the following structure:

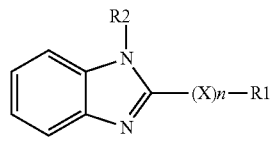

Wherein:

X is an heteroatom selected from among N, S, O, P, SO, $SO_2$ and $SO_3$; preferably from N, S and $SO_3$, and most preferably from N and $SO_3$;

n is 0 or 1;

R1 is a group selected from:

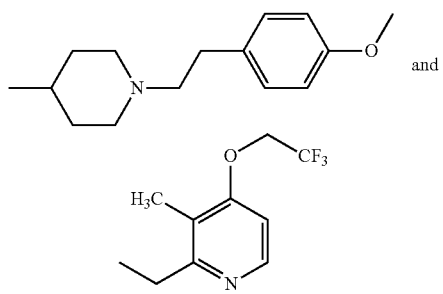

R2 is a group selected from H and:

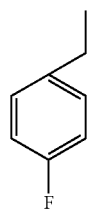

and said pharmaceutical formulation serves as a tracer and is labelled as 18F-lansoprazole.

2. The pharmaceutical formulation of claim 1, wherein the formulation is radioactively marked with elements that emit gamma rays or positrons.

3. The pharmaceutical formulation of claim 2, where said elements that emit gamma rays or positrons are selected from the group consisting of $^{99m}$Tc, $^{111}$In, $^{67}$Ga, $^{201}$Tl, $^{123}$I and $^{133}$Xe, $^{11}$C, $^{13}$N, $^{15}$O and $^{18}$F, and $^{3}$H.

4. The pharmaceutical formulation of claim 1, wherein said benzimidazoles are prepared with an excipient, preservative or other inactive substance that prevents said benzimidazoles from degradation.

5. The pharmaceutical formulation of claim 1, wherein said benzimidazoles are prepared with an excipient, preservative or other inactive substance that allows delivery of a proper effective dose with acceptable or minimal side effects.

6. The pharmaceutical formulation of claim 1, wherein said formulation is radioactively marked.

7. The pharmaceutical formulation of claim 1, wherein said formulation includes a radiotracer for neuroimaging patients.

8. The pharmaceutical formulation of claim 7 wherein said radiotracer is used to diagnose patients with a history of neurodegenerative disorders and tau pathologies, and preferably Alzheimer's Disease.

9. The pharmaceutical formulation of claim 1, wherein said formulation is useful as a diagnostic agent.

10. The pharmaceutical formulation of claim 1, wherein said formulation is useful as a marker for tau protein and structures with tau protein or peptides derived from tau protein, preferably Paired Helical Filaments (PHFs) and neurofibrillary tangles.

11. The pharmaceutical formulation of claim 1, wherein said formulation is useful as a marker for pathological variants of the tau protein.

12. The pharmaceutical formulation of claim 1, wherein said formulation is to diagnose Alzheimer's Disease.

13. The pharmaceutical formulation of claim 1, wherein the benzimidazole-derived compounds are with Astemizole or Lansoprazole,

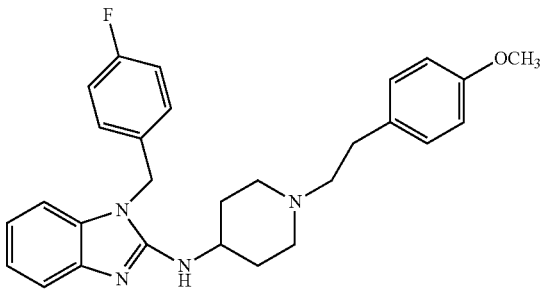

PM: 458,57
Astemizole

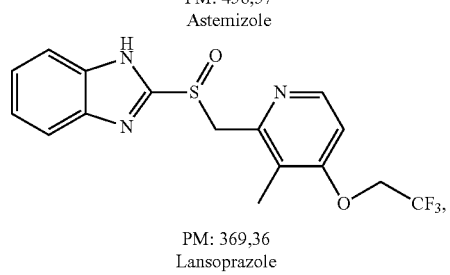

PM: 369,36
Lansoprazole characterized in that they can be used to produce a formulation that is useful as a specific marker for neurodegenerative disorders and tau pathologies, preferably Alzheimer's disease.

14. The pharmaceutical formulation of claim 1, wherein said formulation is useful as a specific marker for cerebral tau aggregates in neurodegenerative disorders and tau pathologies.

15. The pharmaceutical formulation of claim 1, wherein the neuroimaging is Computerized Axial Tomography, Nuclear Magnetic Resonance (NMR), both structural (sNMR) and functional (fNMR), Single Photon Emission Tomography (SPECT), or Positron Emission Tomography (PET).

* * * * *